(12) United States Patent
Holman et al.

(10) Patent No.: US 11,826,066 B2
(45) Date of Patent: *Nov. 28, 2023

(54) FORCEPS WITH INTENTIONALLY MISALIGNED PIN

(71) Applicant: GYRUS ACMI, INC., Westborough, MA (US)

(72) Inventors: Thomas J. Holman, Princeton, MN (US); Riyad Moe, Madison, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 17/462,291

(22) Filed: Aug. 31, 2021

(65) Prior Publication Data

US 2021/0386446 A1    Dec. 16, 2021

Related U.S. Application Data

(63) Continuation of application No. 16/829,182, filed on Mar. 25, 2020, now Pat. No. 11,129,632.

(Continued)

(51) Int. Cl.
*A61B 17/29*    (2006.01)
*A61B 17/28*    (2006.01)
(Continued)

(52) U.S. Cl.
CPC ........ *A61B 17/282* (2013.01); *A61B 17/1285* (2013.01); *A61B 17/2804* (2013.01);
(Continued)

(58) Field of Classification Search
CPC .......... A61B 17/282; A61B 2017/2936; A61B 2017/2933; A61B 2017/2934;
(Continued)

(56) References Cited

U.S. PATENT DOCUMENTS 4,887,612 A   12/1989  Esser et al.
5,009,661 A    4/1991  Michelson
(Continued)

FOREIGN PATENT DOCUMENTS

CN    113966200 A    1/2022
CN    114206239 A    3/2022
(Continued)

OTHER PUBLICATIONS

U.S. Appl. No. 16/829,182 U.S. Pat. No. 11,129,632, filed Mar. 25, 2020, Forceps with Intentionally Misaligned Pin.
(Continued)

*Primary Examiner* — Majid Jamialahmadi
(74) *Attorney, Agent, or Firm* — Schwegman Lundberg & Woessner, P.A.

(57) ABSTRACT

A forceps having at least a first jaw with a longitudinal axis is disclosed. The first jaw can include a body portion, a first flange, a second flange and a cam pin. The first flange can define a first cam slot with a longitudinal extent along the longitudinal axis. The second flange can be spaced from the first flange a distance transverse to the longitudinal axis of the first jaw and can have a second cam slot. The cam pin, with a longitudinal axis, can be moveably secured within the first cam slot and the second cam slot. A diameter of the cam pin can be less than a width between a first longitudinal edge that defines a first side of each of the first cam slot and the second cam slot and a second longitudinal edge that defines a second opposing side of each of the first cam slot and the second cam slot so that the cam pin is moveably received by both the first cam slot and the second cam slot. With the first jaw pivoted to at least a first position, the cam pin and first flange can be configured such that the first longitudinal edge is contacted by the cam pin but the second longitudinal edge is spaced from the cam pin. The cam pin and second flange (Continued)

can be configured such that the first longitudinal edge is spaced from the cam pin but the second longitudinal edge is contacted by the cam pin.

17 Claims, 8 Drawing Sheets

Related U.S. Application Data

(60) Provisional application No. 62/994,220, filed on Mar. 24, 2020, provisional application No. 62/841,476, filed on May 1, 2019, provisional application No. 62/826,532, filed on Mar. 29, 2019, provisional application No. 62/826,522, filed on Mar. 29, 2019.

(51) Int. Cl.
*A61B 18/14* (2006.01)
*A61B 17/128* (2006.01)
*A61B 90/00* (2016.01)
*A61B 17/285* (2006.01)
*B23K 26/21* (2014.01)
*A61B 17/32* (2006.01)
*A61B 17/295* (2006.01)
*A61B 18/00* (2006.01)

(52) U.S. Cl.
CPC ........ *A61B 17/285* (2013.01); *A61B 17/2833* (2013.01); *A61B 17/2909* (2013.01); *A61B 18/149* (2013.01); *A61B 18/1445* (2013.01); *A61B 90/03* (2016.02); *B23K 26/21* (2015.10); *A61B 17/29* (2013.01); *A61B 17/295* (2013.01); *A61B 18/1442* (2013.01); *A61B 18/1447* (2013.01); *A61B 2017/2845* (2013.01); *A61B 2017/2901* (2013.01); *A61B 2017/2902* (2013.01); *A61B 2017/292* (2013.01); *A61B 2017/2903* (2013.01); *A61B 2017/2908* (2013.01); *A61B 2017/2912* (2013.01); *A61B 2017/2916* (2013.01); *A61B 2017/2917* (2013.01); *A61B 2017/2919* (2013.01); *A61B 2017/2925* (2013.01); *A61B 2017/2926* (2013.01); *A61B 2017/2933* (2013.01); *A61B 2017/2936* (2013.01); *A61B 2017/2945* (2013.01); *A61B 2017/2946* (2013.01); *A61B 2017/2947* (2013.01); *A61B 2017/2948* (2013.01); *A61B 2017/320052* (2013.01); *A61B 2017/320095* (2017.08); *A61B 2018/0063* (2013.01); *A61B 2018/0091* (2013.01); *A61B 2018/00148* (2013.01); *A61B 2018/00196* (2013.01); *A61B 2018/00202* (2013.01); *A61B 2018/00309* (2013.01); *A61B 2018/00345* (2013.01); *A61B 2018/00601* (2013.01); *A61B 2018/00636* (2013.01); *A61B 2018/00916* (2013.01); *A61B 2018/00946* (2013.01); *A61B 2018/00952* (2013.01); *A61B 2018/1412* (2013.01); *A61B 2018/1455* (2013.01); *A61B 2018/1457* (2013.01); *A61B 2090/034* (2016.02)

(58) Field of Classification Search
CPC .... A61B 2017/2932; A61B 2017/2937; A61B 2017/2938; A61B 2017/2939; A61B 2017/2947; A61B 2017/2926
See application file for complete search history.

(56) References Cited

U.S. PATENT DOCUMENTS

| | | |
|---|---|---|
| 5,286,255 A | 2/1994 | Weber |
| 5,354,313 A | 10/1994 | Boebel |
| 5,413,583 A | 5/1995 | Wohlers |
| 5,556,416 A | 9/1996 | Clark et al. |
| 5,562,699 A | 10/1996 | Heimberger et al. |
| 5,653,721 A | 8/1997 | Knodel et al. |
| 5,683,412 A | 11/1997 | Scarfone |
| 5,776,130 A | 7/1998 | Buysse et al. |
| 5,782,749 A | 7/1998 | Riza |
| 5,947,984 A | 9/1999 | Whipple |
| 6,039,733 A | 3/2000 | Buysse et al. |
| 6,458,130 B1 | 10/2002 | Frazier et al. |
| 6,585,735 B1 | 7/2003 | Frazier et al. |
| 6,682,544 B2 | 1/2004 | Mastri et al. |
| 6,752,823 B2 | 6/2004 | Prestel |
| 7,083,618 B2 | 8/2006 | Couture et al. |
| 7,118,587 B2 | 10/2006 | Dycus et al. |
| 7,131,971 B2 | 11/2006 | Dycus et al. |
| 7,481,810 B2 | 1/2009 | Dumbauld et al. |
| 7,597,693 B2 | 10/2009 | Garrison |
| 7,604,634 B2 | 10/2009 | Hooven |
| 7,628,791 B2 | 12/2009 | Garrison et al. |
| 8,475,453 B2 | 7/2013 | Marczyk et al. |
| 8,523,893 B2 | 9/2013 | Kessler |
| 8,540,711 B2 | 9/2013 | Dycus et al. |
| 8,632,539 B2 | 1/2014 | Twomey et al. |
| 8,663,270 B2 | 3/2014 | Donnigan et al. |
| 8,672,935 B2 | 3/2014 | Okada et al. |
| 8,702,749 B2 | 4/2014 | Twomey |
| 8,715,277 B2 | 5/2014 | Weizman |
| 8,734,443 B2 | 5/2014 | Hixson et al. |
| 8,968,311 B2 | 3/2015 | Allen, IV et al. |
| 8,968,313 B2 | 3/2015 | Larson |
| 9,113,940 B2 | 8/2015 | Twomey |
| 9,399,508 B2 | 7/2016 | Lakic et al. |
| 9,592,089 B2 | 3/2017 | Lyons et al. |
| 9,636,169 B2 | 5/2017 | Allen, IV et al. |
| 9,668,807 B2 | 6/2017 | Sims et al. |
| 9,681,883 B2 | 6/2017 | Windgassen et al. |
| 9,820,765 B2 | 11/2017 | Allen, IV et al. |
| 9,839,471 B2 | 12/2017 | O'neill et al. |
| 9,861,378 B2 | 1/2018 | Allen, IV et al. |
| 9,867,658 B2 | 1/2018 | Larson et al. |
| 10,349,963 B2 | 7/2019 | Fiksen et al. |
| 10,849,641 B2 | 12/2020 | Boone et al. |
| 11,129,632 B2 | 9/2021 | Holman et al. |
| 2006/0235438 A1 | 10/2006 | Huitema et al. |
| 2009/0112206 A1 | 4/2009 | Dumbauld et al. |
| 2009/0270896 A1 | 10/2009 | Sullivan et al. |
| 2010/0057085 A1 | 3/2010 | Holcomb et al. |
| 2011/0184405 A1 | 7/2011 | Mueller |
| 2013/0085491 A1 | 4/2013 | Twomey et al. |
| 2013/0131666 A1 | 5/2013 | Atwell et al. |
| 2014/0025071 A1 | 1/2014 | Sims et al. |
| 2014/0276803 A1* | 9/2014 | Hart ................. A61B 18/1445 606/45 |
| 2016/0008054 A1 | 1/2016 | Sims et al. |
| 2016/0074101 A1 | 3/2016 | Anglese et al. |
| 2016/0338764 A1 | 11/2016 | Krastins et al. |
| 2017/0196625 A1 | 7/2017 | Nagtegaal |
| 2017/0245921 A1 | 8/2017 | Joseph et al. |
| 2017/0354456 A1 | 12/2017 | Fiksen et al. |
| 2018/0103973 A1 | 4/2018 | Allen, IV et al. |
| 2019/0015124 A1 | 1/2019 | Williams et al. |
| 2019/0175256 A1 | 6/2019 | Butler |
| 2019/0298399 A1 | 10/2019 | Boone et al. |
| 2020/0305901 A1 | 10/2020 | Fiksen et al. |
| 2020/0305902 A1 | 10/2020 | Ward et al. |
| 2020/0305904 A1 | 10/2020 | Holman et al. |
| 2020/0305905 A1 | 10/2020 | Fiksen et al. |
| 2020/0305907 A1 | 10/2020 | Ward |
| 2020/0305909 A1 | 10/2020 | Mensch et al. |
| 2020/0305910 A1 | 10/2020 | Mensch et al. |
| 2020/0305911 A1 | 10/2020 | Pham et al. |
| 2020/0305912 A1 | 10/2020 | Blus et al. |

(56) References Cited

U.S. PATENT DOCUMENTS

| | | | |
|---|---|---|---|
| 2020/0305916 A1 | 10/2020 | Butler et al. |
| 2020/0305917 A1 | 10/2020 | Ward et al. |
| 2020/0305958 A1 | 10/2020 | Ward et al. |
| 2020/0305959 A1 | 10/2020 | Ward et al. |
| 2020/0305960 A1 | 10/2020 | Butler et al. |
| 2020/0305962 A1 | 10/2020 | Ward et al. |
| 2020/0305965 A1 | 10/2020 | Pham et al. |
| 2021/0000536 A1 | 1/2021 | Davies et al. |

FOREIGN PATENT DOCUMENTS

| | | | |
|---|---|---|---|
| CN | 114269268 | A | 4/2022 |
| CN | 114554983 | A | 5/2022 |
| EP | 2347725 | A1 | 7/2011 |
| EP | 2659848 | A2 | 11/2013 |
| EP | 2974685 | A1 | 1/2016 |
| JP | 2022527801 | A | 6/2022 |
| JP | 2022527952 | A | 6/2022 |
| JP | 2022527953 | A | 6/2022 |
| JP | 2022528868 | A | 6/2022 |
| WO | WO-2009070780 | A1 | 6/2009 |
| WO | WO-2016100667 | A2 | 6/2016 |
| WO | WO-2020205372 | A1 | 10/2020 |
| WO | WO-2020205374 | A1 | 10/2020 |
| WO | WO-2020205380 | A1 | 10/2020 |
| WO | WO-2020205381 | A1 | 10/2020 |

OTHER PUBLICATIONS

"Costa Rica Application Serial No. 2021-0537, Office Action dated Feb. 14, 2022", with machine translation, 5 pgs.
"Costa Rican Application Serial No. 2021-0536, Office Action dated Feb. 14, 2022", with machine translation, 5 pgs.
"Costa Rican Application Serial No. 2021-0536, Office Action dated Oct. 27, 2021", with machine translation, 3 pgs.
"Costa Rican Application Serial No. 2021-0537, Office Action dated Oct. 29, 2021", with machine translation, 3 pgs.
"Costa Rican Application Serial No. 2021-0537, Response filed Dec. 22, 2021 to Office Action dated Oct. 29, 2021", with machine translation, 30 pgs.
"Dominican Republic Application Serial No. P2021-0203, Office Action dated Oct. 1, 2021", with machine translation, 3 pgs.
"Dominican Republic Application Serial No. P2021-0204, Office dated mailed Oct. 12, 2021", with machine translation, 3 pgs.
"International Application Serial No. PCT/US2020/024740, International Preliminary Report on Patentability dated Oct. 14, 2021", 8 pgs.
"International Application Serial No. PCT/US2020/024744, International Preliminary Report on Patentability dated Oct. 14, 2021", 10 pgs.
"International Application Serial No. PCT/US2020/024764, International Preliminary Report on Patentability dated Oct. 14, 2021", 8 pgs.
"International Application Serial No. PCT/US2020/024775, International Preliminary Report on Patentability dated Oct. 14, 2021", 9 pgs.
"Mexican Application Serial No. MX/a/2021/011966, Office Action dated Oct. 22, 20221", with machine translation, 9 pgs.
"Mexican Application Serial No. MX/a/2021/011966, Response filed Nov. 30, 2021 to Office Action dated Oct. 22, 2021", with machine translation, 9 pgs.
"Mexican Application Serial No. MX/a/2021/011967, Office Action dated Oct. 22, 2021", with machine translation, 9 pgs.
"Mexican Application Serial No. MX/a/2021/011967, Response filed Nov. 30, 2021 to Office Action dated Oct. 22, 2021", with machine translation, 9 pgs.
"U.S. Appl. No. 16/829,182, 312 Amendment filed Aug. 2, 2021", 8 pgs.
"U.S. Appl. No. 16/829,182, 312 Amendment filed Aug. 24, 2021", 8 pgs.
"U.S. Appl. No. 16/829,182, Notice of Allowance dated Jun. 1, 2021", 12 pgs.
"U.S. Appl. No. 16/829,182, PTO Response to Rule 312 Communication dated Aug. 13, 2021", 2 pgs.
"U.S. Appl. No. 16/829,182, PTO Response to Rule 312 Communication dated Aug. 30, 2021", 2 pgs.
"U.S. Appl. No. 16/830,140, Notice of Allowance dated Jun. 11, 2021", 11 pgs.
"U.S. Appl. No. 16/830,140, Supplemental Notice of Allowability dated Jun. 28, 2021", 6 pgs.
"International Application Serial No. PCT/US2020/024740, International Search Report dated Jun. 16, 2020", 4 pgs.
"International Application Serial No. PCT/US2020/024740, Written Opinion dated Jun. 16, 2020", 6 pgs.
"International Application Serial No. PCT/US2020/024744, International Search Report ated Jul. 6, 2020", 4 pgs.
"International Application Serial No. PCT/US2020/024744, Written Opinion dated Jul. 6, 2020", 8 pgs.
"International Application Serial No. PCT/US2020/024764, International Search Report dated Jun. 18, 2020", 4 pgs.
"International Application Serial No. PCT/US2020/024764, Written Opinion dated Jun. 18, 2020", 6 pgs.
"International Application Serial No. PCT/US2020/024775, International Search Report dated Jul. 21, 2020", 7 pgs.
"International Application Serial No. PCT/US2020/024775, Written Opinion dated Jul. 21, 2020", 7 pgs.
"Chinese Application Serial No. 202080025287.7, Voluntary Amendment filed Jul. 22, 2022", w/ English claims, 13 pgs.
"Chinese Application Serial No. 202080026544.9, Voluntary Amendment filed Jun. 20, 2022", with English translation of claims, 11 pgs.
"Dominican Republic Application Serial No. P2021-0203, Response filed Apr. 20, 2022 to Office Action dated Oct. 1, 2021", with machine translation, 8 pgs.
"Dominican Republic Application Serial No. P2021-0204, Response filed Apr. 20, 2022 to Office Action dated Oct. 12, 2021", with machine translation, 12 pgs.
"European Application Serial No. 20720253.2, Communication Pursuant to Article 94(3) EPC dated Apr. 5, 2023", 4 pgs.
"European Application Serial No. 20720253.2, Response filed May 17, 2022", 13 pgs.
"European Application Serial No. 20720261.5, Response filed May 13, 2022", 10 pgs.

* cited by examiner

FORCEPS WITH INTENTIONALLY MISALIGNED PIN

PRIORITY CLAIM

This application is a Continuation of U.S. patent application Ser. No. 16/829,182 filed Mar. 25, 2020, entitled, "FORCEPS WITH INTENTIONALLY MISALIGNED PIN", which claims priority to U.S. Ser. No. 62/826,532, filed on Mar. 29, 2019, entitled "BLADE ASSEMBLY FOR FORCEPS"; U.S. Ser. No. 62/826,522 filed on Mar. 29, 2019, entitled "SLIDER ASSEMBLY FOR FORCEPS"; U.S. Ser. No. 62/841,476, filed on May 1, 2019, entitled "FORCEPS WITH CAMMING JAWS"; and U.S. Ser. No. 62/994,220, filed Mar. 24, 2020, entitled "FORCEPS DEVICES AND METHODS", the disclosures of each of which are incorporated by reference in their entireties.

TECHNICAL FIELD

This document pertains generally, but not by way of limitation, to surgical devices such as a forceps device, and more particularly, to a forceps device having an actuatable jaw that has a stabilized cam pin.

BACKGROUND

This disclosure relates to surgical devices such as a forceps device. Forceps devices (hereinafter referred to simply as forceps), including but not limited to electrosurgical forceps, are often used for surgical procedures such as laparoscopic surgeries. The forceps can be used to manipulate, engage, grasp, or otherwise interact with anatomical features, such as a vessel or other tissue.

Forceps can include an end effector that is one or more of: rotatable, openable, closeable, extendable, and capable of supplying electromagnetic energy. For example, jaws located at a distal end of the forceps can be actuated via elements at a handpiece of the forceps to cause the jaws to open and close to engage a vessel or other tissue. Forceps may also include a blade, or other end effector type device.

OVERVIEW

Illustrative forceps having an actuatable jaw or jaws facilitated by one or more of flanges with cam slots, a misaligned cam pin and/or a misaligned pivot pin are described herein. The present inventors have recognized there is a need for improved forceps by reducing wobble of the jaws, for example. Thus, the present inventors have recognized various examples to stabilize the jaws to reduce wobble.

Example 1 is a forceps that can optionally include a first jaw. The first jaw can have a longitudinal axis. The first jaw can optionally include a body portion, a first flange, a second flange and a cam pin. The first flange can be coupled to the body portion and can define a first cam slot with a longitudinal extent along the longitudinal axis. The second flange can be coupled to the body portion and spaced from the first flange a distance transverse to the longitudinal axis of the first jaw. The second flange can have a second cam slot. The cam pin can have a longitudinal axis. The cam pin can be moveably secured within the first cam slot and the second cam slot. A diameter of the cam pin can be less than a width between a first longitudinal edge that defines a first side of each of the first cam slot and the second cam slot and a second longitudinal edge that defines a second opposing side of each of the first cam slot and the second cam slot so that the cam pin is moveably received by both the first cam slot and the second cam slot. Optionally, with the first jaw pivoted to at least a first position, the cam pin and first flange can be configured such that the first longitudinal edge can be contacted by the cam pin but the second longitudinal edge can be spaced from the cam pin, and wherein the cam pin and second flange can be configured such that the first longitudinal edge can be spaced from the cam pin but the second longitudinal edge can be contacted by the cam pin.

Example 2 is the forceps of Example 1, wherein the first flange and the second flange can be configured such that the longitudinal axis of the cam pin is one of offset or angled from an axis perpendicular to the longitudinal axis of the first jaw.

Example 3 is the forceps of any one of Examples 1-2, wherein first flange and the second flange can be arranged to extend substantially parallel to one another and each can have a longitudinal extent parallel with and along the longitudinal axis of the first jaw.

Example 4 is the forceps of any one of Examples 1-3, wherein the first flange can be configured to offset at least a portion of the first slot in a first direction relative to the axis perpendicular to the longitudinal axis and the second flange, and wherein the second flange can be configured to offset at least a portion of the second slot in a second direction, opposite the first direction, relative to the axis perpendicular to the longitudinal axis.

Example 5 is the forceps of any one of Examples 1-4, wherein the first flange can be differently configured relative to the second flange to provide the first cam slot with at least one of a different size, shape or orientation with respect to the second cam slot.

Example 6 is the forceps of any one of Examples 1-5, wherein the cam pin and the first flange can be configured such that the first longitudinal edge can be contacted by the cam pin and the second longitudinal edge can be spaced from the cam pin for only a portion of the longitudinal extent of the first cam slot.

Example 7 is the forceps of Example 6, wherein the cam pin and the second flange can be configured such that the first longitudinal edge can be spaced from the cam pin and the second longitudinal edge can be contacted by the cam pin for only a portion of the longitudinal extent of the first cam slot.

Example 8 is the forceps of any one of Examples 1-7, wherein the first flange can have a first aperture spaced from the first cam slot and the second flange can have a second aperture spaced from the second cam slot. The first aperture and the second aperture can be configured to receive a pivot pin that defines a pivot axis for the first jaw to pivot between the first position and a second position, and the first aperture can be offset relative to the second aperture by a distance in a direction that is transverse to the longitudinal axis of the first jaw.

Example 9 is the forceps of any one of Examples 1-7, wherein the first flange can have a first aperture spaced from the first cam slot and the second flange can have a second aperture spaced from the second cam slot, the first aperture and the second aperture can be configured to receive a pivot pin that defines a pivot axis for the first jaw to pivot between the first position and a second position, and the pivot axis can be oriented at a non-parallel orientation with respect to the longitudinal axis of the cam pin.

Example 10 is the forceps of any one of Examples 1-7, further optionally comprising: a first journal coupled to the first flange; a second journal coupled to the second flange;

and a pivot pin received by the first journal and the second journal, wherein the pivot pin can define a pivot axis for the first jaw, and wherein the first journal can be offset relative to the second journal by a distance in a direction that is transverse to the longitudinal axis of the first jaw.

Example 11 is the forceps of any one of Examples 1-10, further optionally comprising: a second jaw having a second longitudinal axis; a third flange coupled to the second jaw and having a third cam slot, wherein the third flange is arranged to extend substantially parallel to the first flange; and a fourth flange spaced from the third flange a distance and coupled to the second jaw, wherein the fourth flange can have a fourth cam slot and can be arranged to extend substantially parallel to the second flange. Optionally, the cam pin can be moveably secured within the third cam slot and the fourth cam slot, the diameter of the cam pin can be less than a width between a third longitudinal edge that defines a first side of each of the third cam slot and the fourth cam slot and a fourth longitudinal edge that defines a second opposing side of each of the third cam slot and the fourth cam slot so as to be received by both the third cam slot and the fourth cam slot in addition to both the first cam slot and the second cam slot.

Example 12 is the forceps of Example 11, wherein the cam pin and the third flange can be configured such that the cam pin can be spaced from the third longitudinal edge of the third flange but can contact the fourth longitudinal edge of the third flange, and the cam pin and the fourth flange can be configured such that the third longitudinal edge of the fourth flange can be contacted by the cam pin but the cam pin can be spaced from the fourth longitudinal edge of the fourth flange.

Example 13 is the forceps of any one of Examples 11-12, further optionally comprising: a handpiece configured with one or more actuators; a tube coupled to the first and second jaws via the pivot pin that defines the pivot axis for the first jaw about the first flange and the second flange and the second jaw about the third flange and the fourth flange; and a shaft arranged inward of the tube, wherein the shaft can be configured to traverse to move the cam pin back and forth within the first cam slot, the second cam slot, the third cam slot and the fourth cam slot to drive the first and second jaws between an open position and a closed position.

Example 14 is a forceps optionally including a first jaw. The first jaw can have a longitudinal axis. The first jaw can optionally include a first flange, a second flange, a cam pin and a pivot pin. The first flange can be coupled to the first jaw and can have a first cam slot and a first aperture spaced from the first cam slot. The second flange can be spaced from the first flange a distance and can be coupled to the first jaw. The second flange can define a second cam slot. The cam pin can be moveably secured within the first cam slot and the second cam slot and can have a diameter less than a width of both the first cam slot and the second cam slot so as to be received by both the first cam slot and the second cam slot. The pivot pin can be coupled with the first flange and the second flange via the first aperture and the second aperture and can define a pivot axis for the first jaw about the first flange and the second flange. The pivot axis can be oriented at a non-parallel orientation with respect to a longitudinal axis of the cam pin.

Example 15 is the forceps of Example 14, wherein one of the pivot axis of the pivot pin or the longitudinal axis of the cam pin can be angled with respect to an axis perpendicular to and intersecting with the longitudinal axis of the first jaw.

Example 16 is the forceps of Example 14, wherein, with the first jaw pivoted to at least a first position about the pivot pin and the cam pin received in the first cam slot, the first jaw and cam pin can be configured such that the cam pin can be spaced from a first edge of the first flange that defines a first side of the first cam slot but contacts a second edge of the first flange that defines a second side of the first cam slot, the second side opposing the first side.

Example 17 is the forceps of any one of Examples 14-16, wherein the cam pin and second flange can be configured such that a first longitudinal edge of the second flange that defines the second cam slot can be spaced from the cam pin but a second longitudinal edge opposing the first longitudinal edge across the second cam slot can be contacted by the cam pin Example 18 is a forceps that optionally includes a first jaw with a longitudinal axis. The first jaw can have a first cam slot with a longitudinal extent along the longitudinal axis. The first jaw can have a cam pin moveably secured within the first cam slot and having a longitudinal axis. Optionally, with the first jaw pivoted to at least a first position and the cam pin can be received in the first cam slot, the first jaw and the cam pin can be configured such that the cam pin can be spaced from a first edge of the first jaw that defines a first side of the first cam slot but can contact a second edge of the first jaw that defines a second side of the first cam slot, the second side opposing the first side. A centerline axis of the first cam slot can be angled relative to the longitudinal axis of the cam pin such that the cam pin can be misaligned with the first cam slot.

Example 19 is the forceps of Example 18, wherein the centerline axis of first cam slot can be offset from the longitudinal axis of the cam pin such that the cam pin can be misaligned with the first cam slot.

Example 20 is the forceps of any one of Examples 18-19, wherein the first jaw can have a first aperture spaced from the first cam slot, the first aperture can be configured to receive a pivot pin that defines a pivot axis for the first jaw to pivot between the first position and a second position. The pivot axis can be oriented at a non-parallel orientation with respect to the longitudinal axis of the cam pin.

Example 21 is any one or combination of the Examples or elements of the Examples 1-20.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

The present disclosure is directed to a surgical device such as forceps that allows a surgeon to operate an end effector such as jaws of the device. It is contemplated that the disclosed concepts such as the misalignment of the pivot pin and/or cam pin within a respective aperture or relative to one another can be used in other devices and other components besides forceps, surgical devices and end effectors. For example, the forceps and concepts herein are applicable to any type of device, surgical or otherwise, such as devices that facilitate actuation of an end effector(s) or other element(s). Any representation of a forceps or indeed a surgical device or description herein is shown primarily for illustrative purposes to disclose features of various examples and to provide an example of an apparatus that can benefit from the misalignment of the pivot pin and/or cam pin and other concepts disclosed herein.

According to one example, a jaw of the end effector can utilize a pin in a cam slot to open and close the jaw. Some degree of clearance is required between the cam slot and the pin to allow for this movement. However, this clearance can lead to play that results in the jaw wobbling. To address this, some of the play or clearance can be taken up to reduce a wobble of the jaw as will be discussed further herein and illustrated in reference to FIGS. 4A-10. For example, if the jaw has two flanges each with a respective cam slot, the cam pin can be misaligned slightly with a centerline axis of one or more of the cam slots so that the cam pin is placed in contact with an edge or edges of the slots/flanges. Thus, the cam pin can be askew or misaligned within the slot, for example. In an arrangement with two flanges, the cam pin can contact a first longitudinal edge of a first flange that defines of one of the cam slots while the cam pin contacts a second longitudinal edge of a second flange that defines the second one cam slots. Such contact can reduce play and jaw wobbling.

In this disclosure, relative terms, such as, for example, "about", "generally", or "substantially" are used to indicate a possible variation of ±10% in a stated numeric value or within ±10° of the numeric value.

Figure 1:
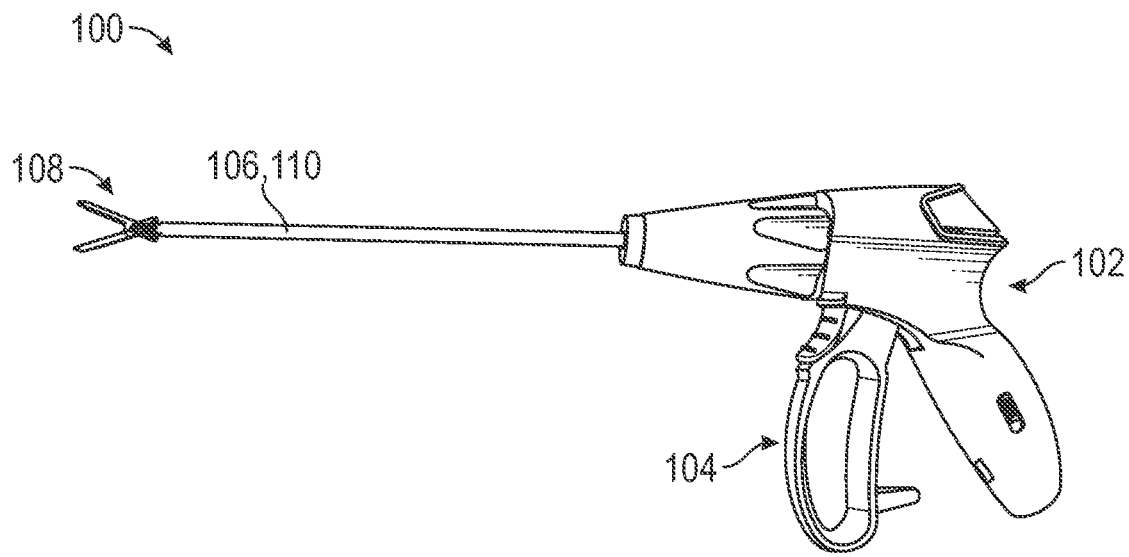
FIG. 1 is a side view of a forceps having jaws according to an example of the present application.

FIG. 1 shows an example of a surgical forceps 100. The surgical forceps 100 can include a handpiece 102, one or more actuators 104, a shaft 106 and an end effector 108.

The handpiece 102 can be coupled to the shaft 106 at a proximal end thereof. The end effector 108 can be moveably coupled to the shaft 106 at a distal end thereof. The shaft 106 can have an elongate extent and can be configured to access a body of a patient for laparoscopic or other treatment using the end effector 108. The one or more actuators 104 can be located at the handpiece 102 and can be coupled to end effector 108 via the shaft 106, which can be configured as a hollow tube 110 allowing for passage of portions of the one or more actuators 104 to the end effector 108. Thus, the one or more actuators 104 can be connected to and can manipulate the end effector 108.

Figure 1A:
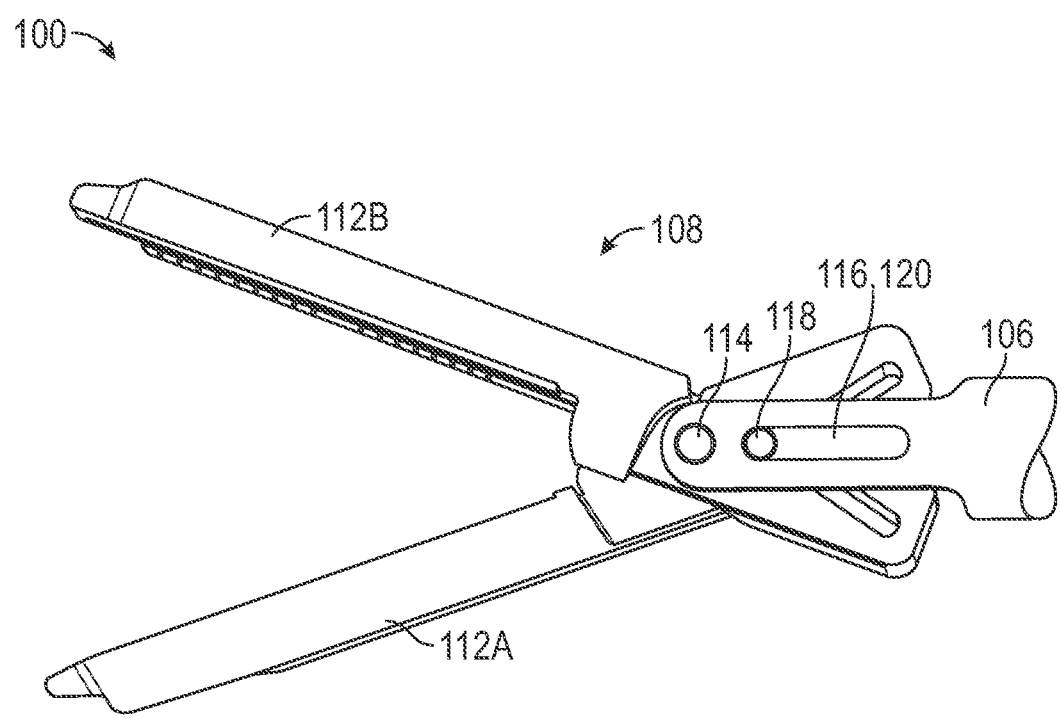
FIG. 1A is an enlarged view of a distal portion of the forceps of FIG. 1 illustrating the jaws and other components according to an example of the present application.

As shown in FIG. 1A, the end effector 108 can be configured as articulating jaws 112A and 112B (double acting jaws) configured to manipulate, engage, grasp, or otherwise interact with anatomical features, such as a vessel or other tissue. The forceps 100 can also be configured as electrosurgical forceps with one or both of the jaws configured to apply an electrical current to the vessel or other tissue to cauterize or otherwise treat the tissue or vessel.

Further details regarding the construction of the surgical forceps 100 can be found in the U.S. Provisional Patent Applications incorporated by reference in their entirety above. Thus, the embodiment of the forceps of FIGS. 1-3B is known from these U.S. Provisional Patent Applicants and is provided herein for background in regard to the operation and construction of the further embodiments of the forceps described in reference to FIGS. 4A-10.

As shown in FIG. 1A, the jaws 112A and 112B of the end effector 108 can be connected to the shaft 106 via a pivot pin 114. The forceps 100 can have a reciprocating inner shaft 116 (part of the one or more actuators 104 of FIG. 1) at least partially positioned within the hollow tube 110 comprising the shaft 106. The inner shaft 116 can have a cam or slot cam pin 118 attached thereto (for example at a distal end thereof). Thus, the inner shaft 116, and the cam pin 118 thereby, can be moveable relative to the outer shaft 106 in a translatable manner. Movement of the inner shaft 116 (visible through the slot 120) can traverse the cam pin 118 in along a longitudinal axis of the outer shaft 106 and longitudinal axis of the jaws 112A and 112B and can move the jaws 112A and 112B as a result of a camming action as further discussed below. It should be noted that the slot 120 may not be needed in all embodiments for function of the forceps 100 and can be provided for manufacturing purposes as discussed in the U.S. Provisional Patent Applications referenced to and incorporated above.

Figure 2:
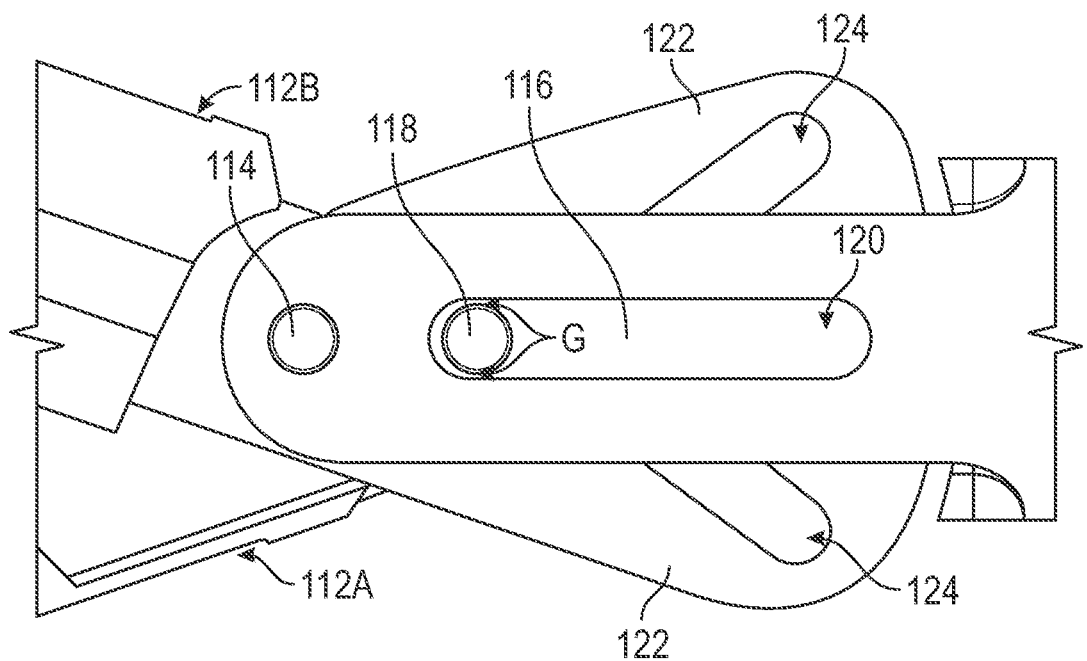
FIG. 2 is yet a further enlarged view of a portion of the forceps showing flanges of the jaws coupled with a shaft of the forceps according to an example of the present application.

FIG. 2 provides an enlarged view of portions of the jaws 112A and 112B, the pivot pin 114, the distal inner shaft 116, the distal shaft 106, the cam pin 118 and the slot 124 with the arrangement and function described above with regard to FIG. 1A.

As shown in FIG. 2, each of the jaws 112A and 112B may have a pair of spaced flanges 122 (only two, one for each of the jaws 112A and 112B are visible in FIG. 2). The arrangement and construction of the flanges 122 will be described in further detail subsequently. According to some examples, the pair of flanges 122 for the jaw 112A and/or jaw 112B can be arranged generally parallel with one another (e.g., having interfacing generally parallel spaced inner surfaces) along a longitudinal direction but spaced by the inner shaft 116. Each of the pair of flanges 122 can be pivotably coupled to the shaft 106 via the pivot pin 114.

Each of the flanges 122 can also have a slot 124 (sometimes referred to as a cam slot herein) spaced from the pivot pin 114. The slot 124 can be configured to receive the cam pin 118, which can be moveably secured therein. The cam pin 118 can have a diameter less than a width of the slot 124 so as to be moveably received by the slot 124. This difference in a diameter of the cam pin 118 to the width of the slot 124 allows the cam pin 118 of the inner shaft 116 to be moveable along the slot 124 as discussed below. As the inner shaft 116 moves, the cam pin 118 can traverse along a longitudinal length of the slot 124. The cam pin 118 and the inner shaft 116 (part of one or more actuators 104) can be configured for reciprocating movement relative to the shaft 106 such that the cam pin 118 can traverse the slot 124 in a reciprocating manner. Each slot 124 can be configured to work as cam so that as the cam pin 118 traverses the longitudinal length of the slot 124 the jaws are driven from a first open position (shown in FIG. 1A) towards and to a second closed (grasping) position or vice versa. The shape and size of the flanges 122 including the shape, size and arrangement of the slot 124 can be configured to limit or control the degree of contact that other portions of the jaws 112A and/or 112B can have with the vessel or other tissue being treated.

As shown in FIGS. 1A and 2, the slot 124 for each of the pair of flanges 122 can be aligned with one another and can have generally a same shape. Put another way, the slot 124 of each of the pair of flanges 122 can be aligned when viewing the end effector 108 from the side as illustrated in FIGS. 1A and 2. Thus, the slot 124 can be aligned with the slot 124 in a direction perpendicular to a direction of a longitudinal axis of the jaws 112A and 112B (longitudinal axis LA shown in FIGS. 3A, 3B, etc.). Put another way, the slot 124 can be aligned with the opposing slot 124, the direction of this alignment is along an axis of the pivot pin 114. The pivot pin 114 can be secured to the outer frame comprising the outer shaft 106. Pivot bores on the flanges 112A and 112B can be secured to the pivot pin 114. The cam pin 118 can be fitted into the slot 124 on each of the pair of flanges 122.

Figure 2A:
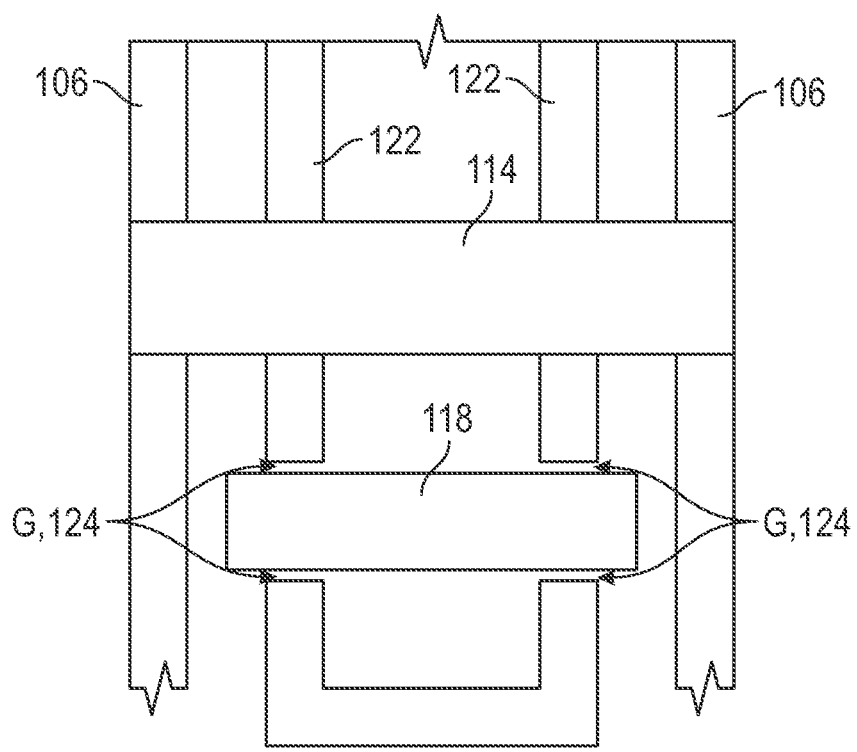
FIG. 2A is a schematic cross-sectional view of the portion of the forceps of FIG. 2 showing the cam pin disposed within the cam slots and the cam slots having gaps of substantially equal size with respect to the cam pin to facilitate movement of the cam pin within the cam slots according to an example of the present application.

As shown particularly in FIGS. 2 and 2A, the pins 114 and 118 can be arranged parallel with one another, the cam slots 124 can be the same size, and can be aligned as discussed above an illustrated. Therefore, there can be an equivalent gap G between the cam pin 118 and either cam slot 124. Furthermore, the gap G can be substantially the same distance between the cam pin 118 and a first longitudinal edge of the slot and a second longitudinal edge of the slot as shown in FIGS. 2 and 2A.

Figure 3A:
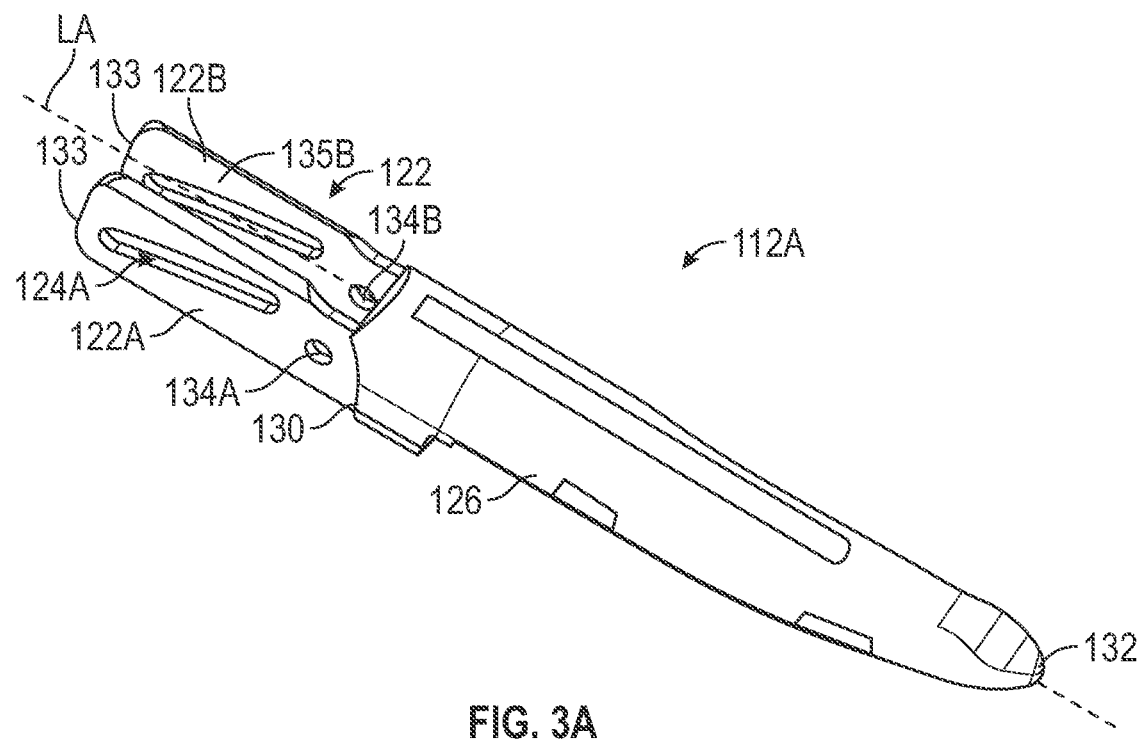
FIGS. 3A and 3B are perspective views of one jaw of the forceps of FIGS. 1-2 shown in isolation from a remainder of the forceps according to an example of the present application.
Figure 3B:
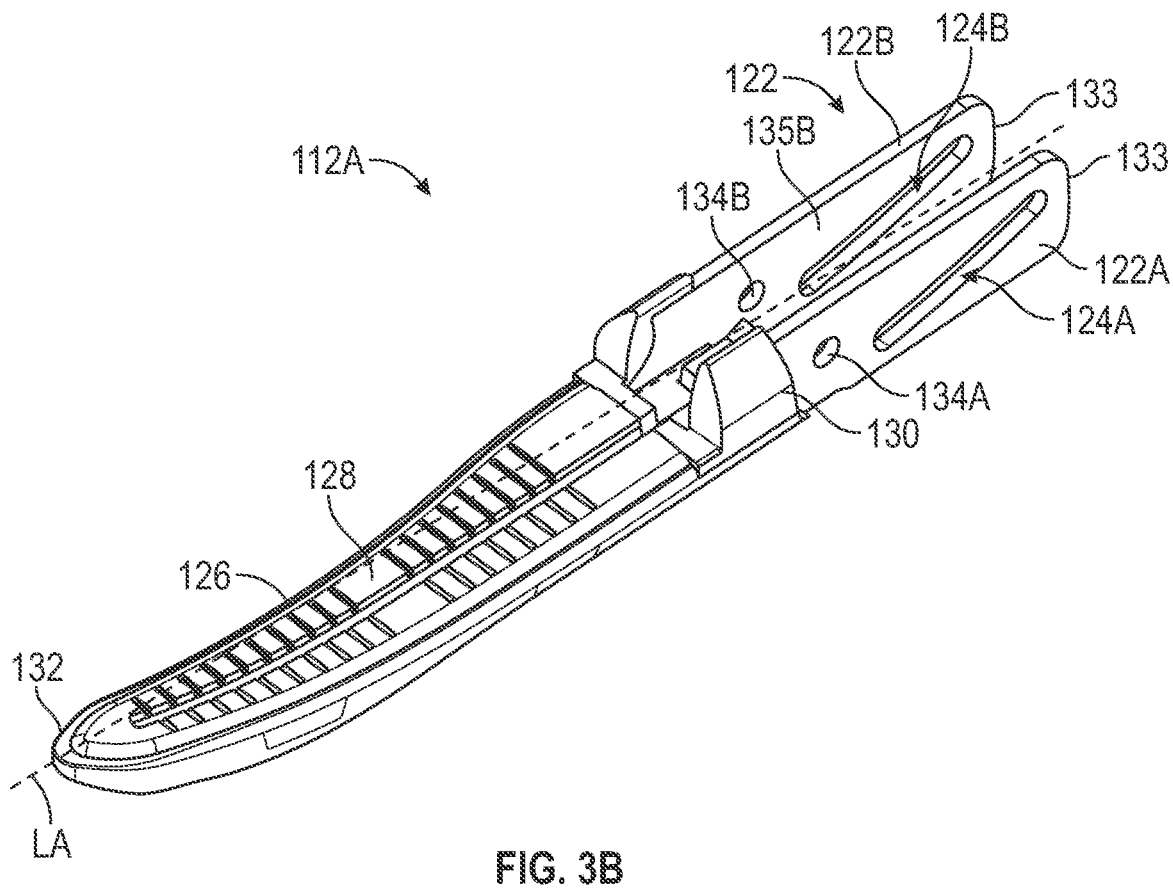

FIG. 2A schematically illustrates the jaw 112A of FIGS. 1A and 2. FIG. 2A shows the pivot pin 114 can be coupled to the outer shaft 106. As discussed previously, the outer shaft 106 can be a stationary tube. The cam pin 118 can be moveably received within the slot 124 of the pair of flanges 122 via the gap G. The slots 124 can be arranged coaxially interfacing one another across from and perpendicular relative the longitudinal axis LA (FIGS. 3A, 3B). As shown in FIG. 2A, the cam pin 118 can be arranged parallel with the pivot pin 114. The cam slots 124 can be a same size and can be aligned as previously described. The gap G can be substantially equivalent (i.e. there can be substantially the same distance between the cam pin 118 and opposing edges of each cam slot 124) for the cam slot 124 and the cam pin 118.

It is understood that various modifications can be made to the surgical forceps described herein. For example, the jaws may not be dual acting according to some examples but can rather be single acting. A single flange can be utilized rather than a pair of flanges in some examples. Although the jaws are described as having a flange (or flanges), in some cases the jaws may not utilize a flange such that features such as the slot 124 can be directly through a body portion of the jaw itself, for example.

FIGS. 3A and 3B show the single jaw 112A comprising one of the jaws 112A and 112B previously described. The jaw 112A can have the pair of flanges 122, a body 126 and a longitudinal axis LA. The flanges 122 can include a first flange 122A and a second flange 122B. The body 126 can include an engaging surface 128 (FIG. 3B), a proximal end 130 and a distal end 132.

The pair of flanges 122 can be coupled to the body 126 at or near the proximal end 130 thereof. The pair of flanges 122 can be integral with the body 126 such that the jaw 112A can comprise a single piece assembly. The body 126 can be configured such as with the engaging surface 128 to manipulate, engage, grasp, or otherwise interact with anatomical features, such as a vessel or other tissue. The engaging surface 128, and indeed the body 126, can include features or components to facilitate this interaction including components and features capable of supplying electromagnetic energy to the vessel or other tissue.

As previously discussed, the first flange 122A and the second flange 122B can be spaced apart from one another a distance to accommodate the inner shaft and other features of the surgical forceps, for example. The first flange 122A and the second flange 122B can extend generally parallel with one another and generally parallel to the longitudinal axis LA. Put another way, the first flange 122A can have an inner surface 135A (FIG. 3A) that interfaces with but is spaced from an inner surface 135B (FIG. 3B) of the second flange 122B. The inner surface 135A can extend substantially parallel with the inner surface 135B. The longitudinal axis LA can extend from the distal end 132 of the body 126 along an elongated extent of the body 126 and can extend along an elongated extent of the first flange 122A and the second flange 122B to a proximal end 133 of each of thereof.

As previously discussed and illustrated, the pair of flanges 122 each have the slot 124 that is defined thereby. For further clarity, the slot 124 is illustrated as first slot 124A (defined by the first flange 122A) and second slot 124B (defined by second flange 122B and numbered only in FIG. 3B) herein. The slot 124A and 124B has an elongate extent (sometimes referred to herein as a length or longitudinal extent) along the longitudinal axis LA and has a width in other directions including a transverse direction to the longitudinal axis LA. The first slot 124A and the second slot 124B can be sized and shaped to receive the cam pin 118 (FIGS. 1A and 2) with the cam pin 118 being moveable such as along the longitudinal axis LA as previously illustrated and discussed.

As shown in FIGS. 3A and 3B, the first flange 122A defines a first aperture 134A and the second flange 122B defines a second aperture 134B. The first aperture 134A can be spaced from the first slot 124A a distance along the longitudinal axis LA. The first aperture 134A can be closer to, or farther from, the body 126 than the first slot 124A, for example. Similarly, the second aperture 134B can be spaced from the second slot 124B a distance along the longitudinal axis LA. The second aperture 134B can be closer to, of farther from, the body 126 than the second slot 124B, for example. The first aperture 134A and the second aperture 134B are configured to receive the pivot pin 114 (FIGS. 1A and 2) as previously discussed and illustrated.

Figure 4A:
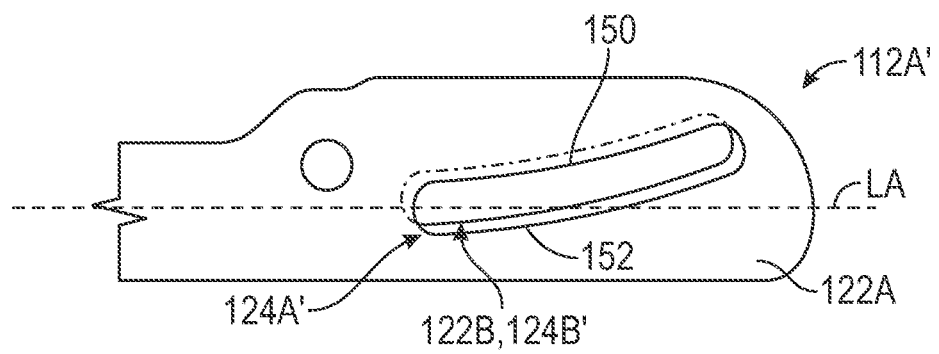
FIG. 4A is a first side view of a portion of a jaw according to a second example, the jaw having a designed offset of a first cam slot of a first flange from a second cam slot of a second flange of the jaw according to an example of the present application.

FIG. 4A shows a portion of a jaw 112A' modified from the jaw 112A previously described. In particular, a first slot 124A' of the first flange 122A can be offset from the second slot 124B' of the second flange 122B. This offset can be a distance in a direction transverse to the longitudinal axis LA, for example. The distance of the offset can be about the longitudinal axis LA but is not necessarily in a direction axially along the longitudinal axis LA. Thus, the offset can be in a plane perpendicular to the longitudinal axis LA with the plane having no extent along the longitudinal axis LA (i.e. the offset can be in a lateral direction having no extent proximal or distal along the jaw 112A'). This offset can be in a direction transverse to the body 126 (FIG. 3B) or an edge of the body 126, for example. Put another way, a first longitudinal edge 150 of the first flange 122A that defines a first side of first slot 124A' can be positioned asymmetrically relative to the longitudinal axis LA as compared with a corresponding third longitudinal edge 154 (shown in FIG. 4B) of the second flange 122B that defines a first side of the second slot 124B'. Similarly, a second longitudinal edge 152 of the first flange 122A that defines a second side (opposing the first side) of first slot 124A' can be positioned asymmetrically relative to the longitudinal axis LA as compared with a corresponding fourth longitudinal edge 156 (shown in FIG. 4B) of the second flange 122B that defines a second side of the second slot 124B' It should be noted that in the example of FIG. 4A, the first slot 124A' and the second slot 124B' can have a same size and shape (e.g. same geometry of an elongate extent and width) but each can have a different positioning relative to the longitudinal axis LA. In some examples, both of the first slot 124A' and the second slot 124B' can be offset the distance transverse to the longitudinal axis LA.

Figure 4B:
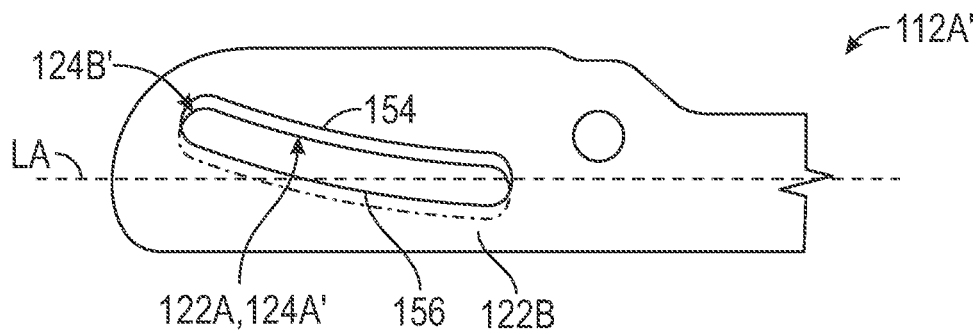
FIG. 4B is a second side view of the portion of the jaw of FIG. 4A from an opposing side thereof.

FIG. 4B shows an opposing side of the jaw 112A' from the view provided in FIG. 4A such that flange 122B is mainly visible. As with FIG. 4A, the first slot 124A' of the first flange 122A (only partially visible in FIG. 4B and with portions indicated in phantom) can be offset as previously described with regard to FIG. 4A.

Figure 5A:
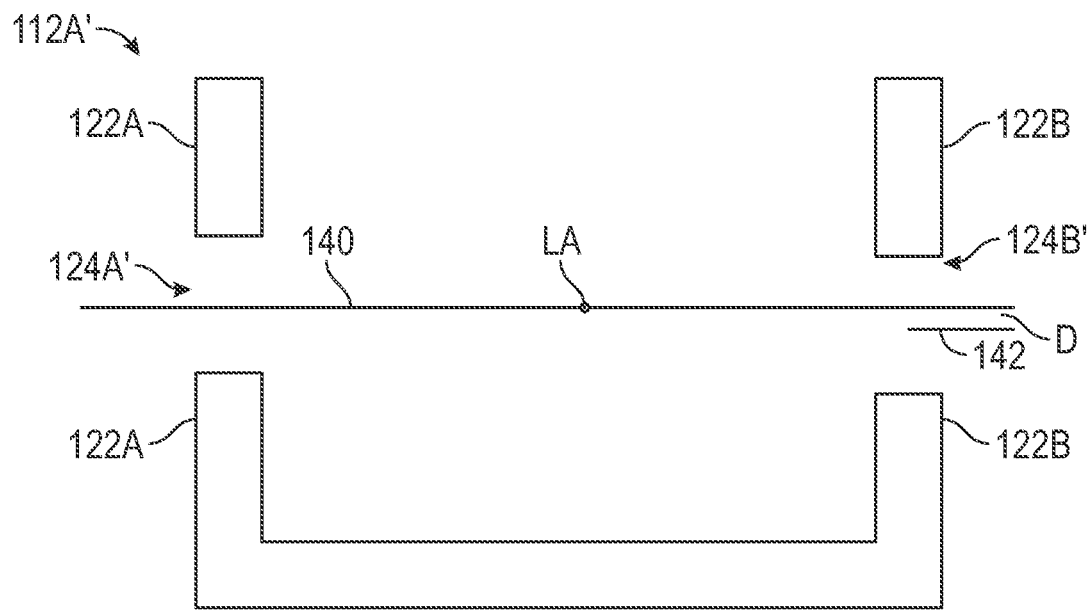
FIG. 5A is a schematic cross-sectional view of the jaw of FIGS. 4A and 4B illustrating the offset in the first cam slot of the first flange of the jaw from the second cam slot of the second flange of the jaw according to an example of the present application.

FIG. 5A schematically illustrates the jaw 112A' with at least one of the first flange 122A and the second flange 122B having the offset previously discussed. In particular the second flange 122B with cam slot 124B' can be provided with the offset of a distance D1. This distance D1 can be between the first slot 124A' and the second slot 124B' and can be relative to the longitudinal axis LA. The offset can be the distance D1 relative to an axis 140 and in a plane transverse to and intersecting with the longitudinal axis LA as indicated in FIG. 5A. The axis 140 can be arranged entirely lateral to the longitudinal axis LA such that the axis 140 has substantially little or no proximal/distal extent along the longitudinal axis LA and relative to the first flange 122A and the second flange 122B. Put another way, a centerline axis 142 of the second cam slot 124B' can be offset the distance D1 in a direction that is transverse to the longitudinal axis LA. The centerline axis 142 of the second cam slot 142 can be offset from a longitudinal axis 144 of the cam pin 118 as further illustrated in FIG. 5B.

Figure 5B:
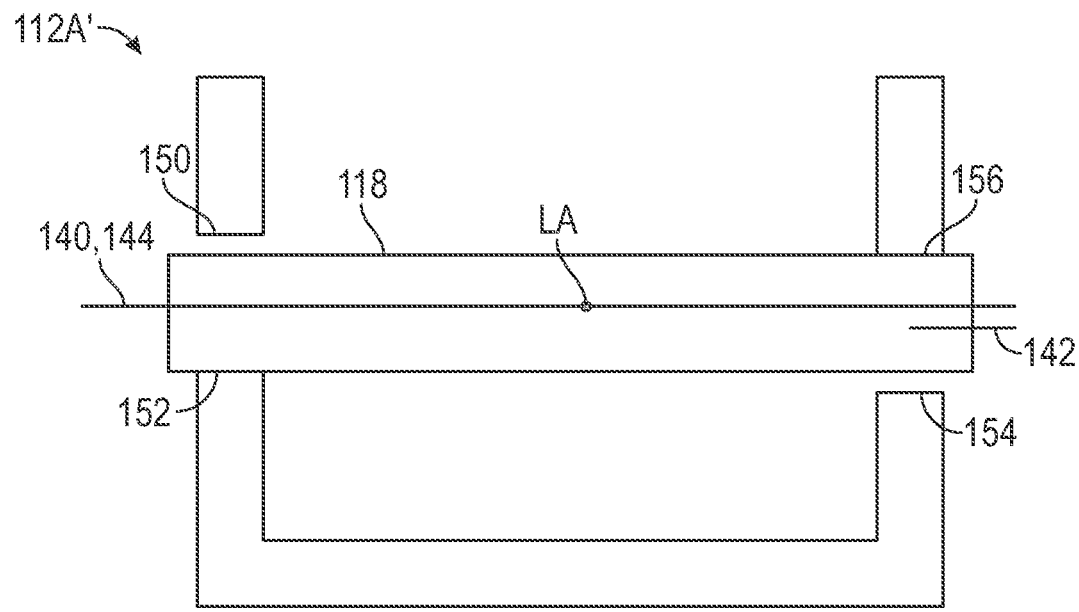
FIG. 5B is a schematic cross-sectional view of the arrangement of FIG. 5A further illustrating a misalignment of a cam pin relative to the first cam slot and the second cam slot that results from the offset of FIGS. 4A and 4B according to an example of the present application.

FIG. 5B illustrates the cam pin 118 positioned within the jaw 112A' in a schematic manner. As a result of the offset of the second slot 124B', the longitudinal axis 144 of the cam pin 118 can be offset within the first slot 124A' and the second slot 124B' such as in the manner illustrated. This offset can be in a direction transverse to the longitudinal axis LA. The offset can be the same as the total amount of gap on a side. However, according to other examples, the offset distance D1 can be one of more or less than the gap on a side.

As illustrated in FIG. 5B, the configuration of the first flange 122A and the second flange 122B with the offset of at least the second slot 124B' can cause the cam pin 118 to be spaced from the first longitudinal edge 150 of the first flange 122A that defines the first side of the first slot 124A' by a gap. The cam pin 118 can contact the second longitudinal edge 152 of the second flange 122B that defines a second opposing side of the first slot 124A'. Similarly, the cam pin 118 can be spaced from the third longitudinal edge 154 of the second flange 122B that defines the first side of the second slot 124B' by a gap. The cam pin 118 can contact the fourth longitudinal edge 156 of the second flange 122B that defines the second opposing side of the second slot 124B'. Contact between the cam pin 118 and the edge 152 and the cam pin 118 and the edge 156 can reduce play and wobble of the jaw 112A'. The cam pin 118 can still move within the first slot 124A' and the second slot 124B' into or out of the page of view because of the clearance between the cam pin 118 and the first longitudinal edge 150 and cam pin 118 the third longitudinal edge 154.

As used herein the term, "centerline axis" connotes an axis that is positioned equidistant from the first side and the second side of the first slot 124A' and/or the second slot 124B'. Thus, the centerline axis 142 can be equidistant from the third longitudinal edge 154 of the second flange 122B and the fourth longitudinal edge 156 of the second flange 122B.

Figure 6A:
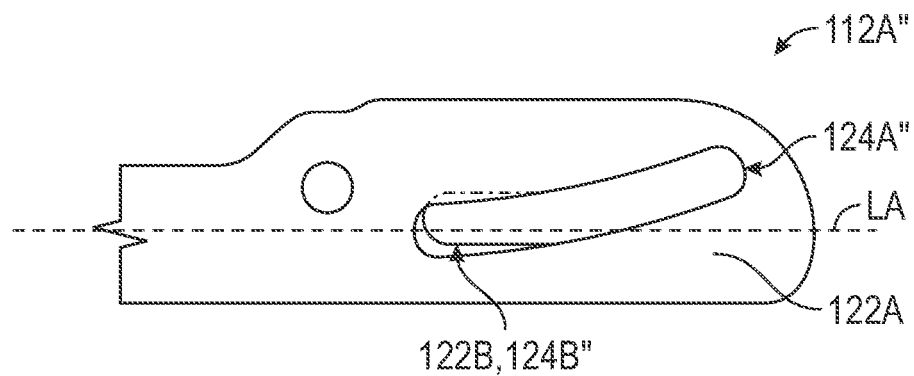
FIG. 6A is a first side view of a portion of a jaw according to a third example, the jaw having a designed offset of a first cam slot of a first flange from a second cam slot of a second flange of the jaw for only a portion of a longitudinal extent of the first cam slot and the second cam slot according to an example of the present application.
Figure 6B:
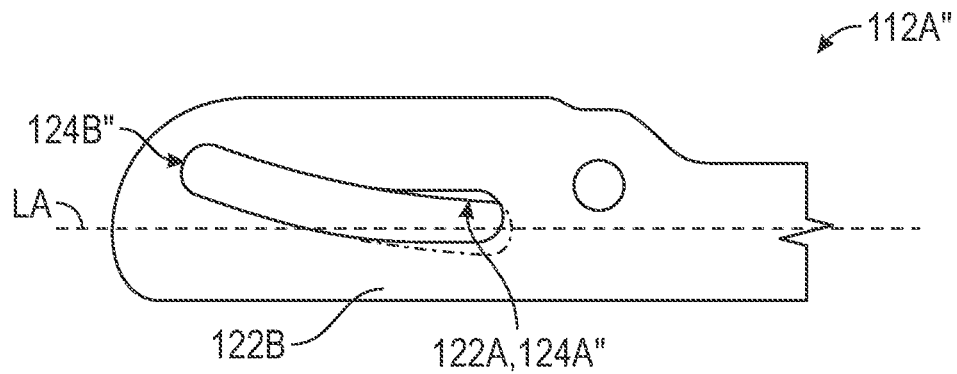
FIG. 6B is a second side view of the portion of the jaw of FIG. 6A from an opposing side thereof

FIGS. 6A and 6B illustrate a jaw 112A" according to another example. In the example of FIGS. 6A and 6B, the jaw 112A" can be constructed in the manner of the jaw 112A' previously described save that only a portion of a longitudinal extent of a cam slot 124A" of the first flange 122A and/or the cam slot 124B" of the second flange 122B can be offset relative to the longitudinal axis LA and/or one another. The configuration of FIGS. 6A and 6B can cause the cam pin to drag on the cam slot through less than the full travel of the cam pin within the slots 124A" and 124B". Put another way, the configuration of FIGS. 6A and 6B (and that of FIGS. 5A and 5B) can increase the interference between the pin and slot and thereby can increase the stability of the jaw. This can be beneficial because as the jaws close, contact forces rise and therefore drag forces rise too. Thus, the present embodiment recognizes a possible benefit for reduced drag forces nearing jaw closure but can provide for stability/reduced wobble when the jaw(s) are at or nearing a fully open position.

As illustrated in FIGS. 6A and 6B, the cam slots 124A" and 124B" can be misaligned (e.g., offset in a direction perpendicular to the LA of the jaw(s)) for a portion and aligned for a portion of their longitudinal extent. In FIGS. 6A and 6B, the portion of the cam slots 124A" and 124B" related to pin movement near jaw closure can be at a proximal portion of the cam slot 124A" and 124B". As shown in FIGS. 6A and 6B, the slot 124A" and 124B" in this area can be aligned or substantially aligned for this proximal portion. The portion of the slots 124A" and 124B" related to pin movement near jaw opening can be at an opposing distal portion of the cam slots 124A" and 124B" and the slots 124A" and 124B" can be misaligned for this distal portion. For the proximal portion of the slots 124A" and 124A" having alignment, the configuration of the flanges and slots can correspond to the arrangement previously described in FIGS. 1-3B. For the distal portion of the slots 124A" and 124B" the configuration can correspond to the arrangement of FIGS. 4A-5B, for example.

Figure 7:
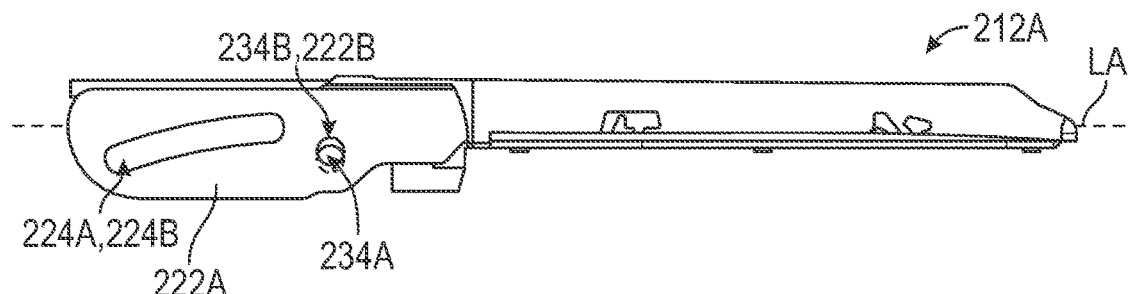
FIG. 7 is a first side view the jaw according to a fourth example, the jaw having an offset of a first pivot aperture of a first flange of the jaw from a second pivot aperture of a second flange of the jaw according to an example of the present application.

FIG. 7 shows a jaw 212A according to another example. The jaw 212A can include a first slot 224A of a first flange 222A and a second slot 224B of a second flange 222B. The first flange 222A can have a first aperture 234A and the second flange 222B can have a second aperture 234B. The first aperture 234A and the second aperture 234B can be constructed in the manner of the first aperture 134A and the second aperture 134B described previously. As such, the first aperture 234A and the second aperture 234B can be configured to receive the pivot pin 114 (FIGS. 1A and 2) as previously discussed and illustrated. However, with the example of FIG. 7, the first aperture 234A can be offset a distance from the second aperture 234B. This offset can be a distance in a direction transverse to the longitudinal axis LA, for example. It should be noted that in the example of FIG. 7, the first aperture 234A and the second aperture 234B can have a same size (e.g. same diameter) but each can have a different positioning relative to the longitudinal axis LA.

Figure 7A:
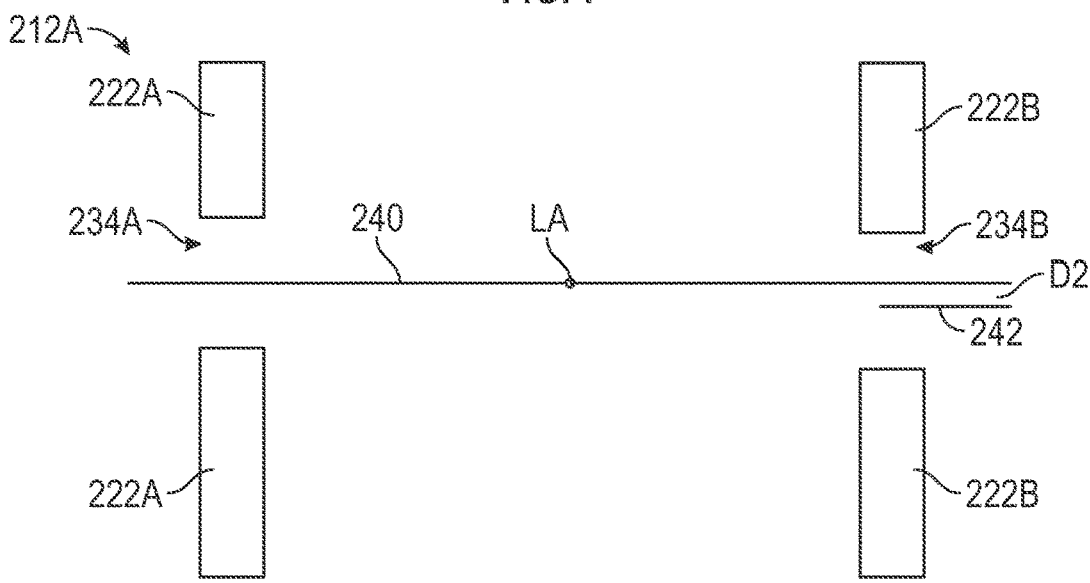
FIG. 7A is a schematic cross-sectional view of the jaw of FIG. 7 illustrating the offset in the first pivot aperture of the first flange of the jaw from the second pivot aperture of the second flange of the jaw according to an example of the present application.

FIG. 7A schematically illustrates the jaw 212A with the first flange 222A and the second flange 222B having the offset of the distance D2 between at least one of the first aperture 234A and the second aperture 234B and relative to an axis transverse to an intersecting the longitudinal axis LA. The offset can be the distance D2 measured from a centerline axis 242 of the aperture 234B, for example, relative to an axis 240 transverse to the longitudinal axis LA as indicated in FIG. 5A.

Figure 7B:
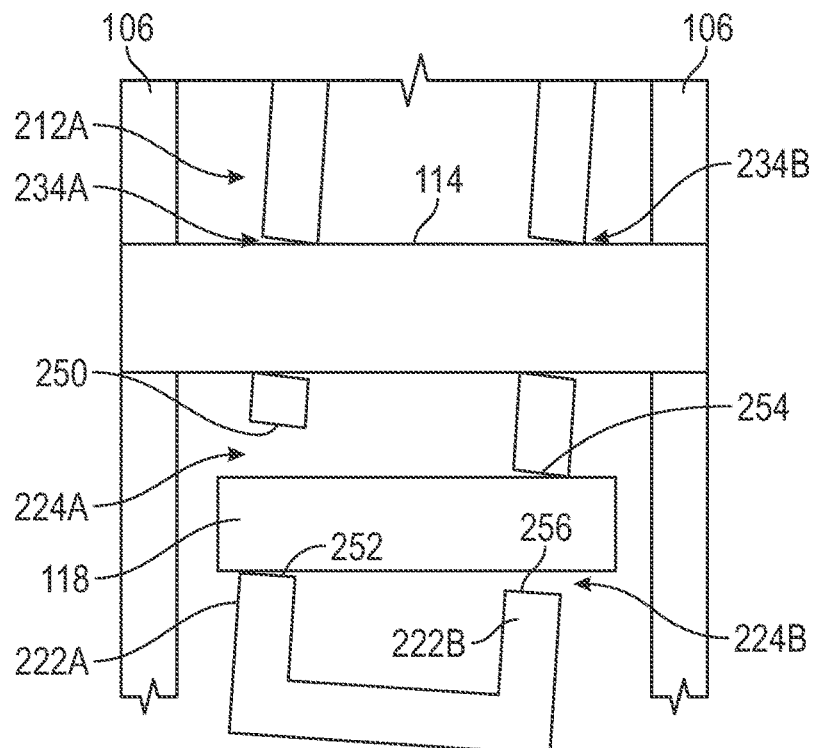
FIG. 7B is a schematic cross-sectional view of the arrangement of FIG. 7A further illustrating a misalignment of a pivot pin and a cam pin that results from the offset of FIG. 7A according to an example of the present application.

FIG. 7B illustrates the pivot pin 114 positioned within the jaw 212A in a schematic manner. As a result of the offset/misalignment of first aperture 234A and/or the second aperture 234B, even though the pivot pin 114 can be square with the outer shaft 106, because the because the pivot bores 234A and 234B are misaligned, the jaw 212A sits tilted, askew on the pivot pin 114. Even though the cam slots 224A and 224B can be aligned with each other, they are not aligned with the cam pin 118, which can be positioned parallel with the pivot pin 114. As such, an edge 252 of the cam slot 224A interacts/contacts the cam pin 118 (but an opposing edge 250 of the cam slot 224A is spaced from the cam pin 118) while a third longitudinal edge of the cam slot 224B interacts/contacts the cam pin 118 (but an opposing fourth longitudinal edge of the cam slot 224B can be spaced from the cam pin 118). Put another way, the cam pin 118 can be positioned within the jaw 212A and can be moveably received by the first slot 224A and the second slot 224B but can be stabilized by interaction with the edges 252 and 254 of the cam slot 224A and 224B much in the manner of the arrangements previously described in FIGS. 4A-6B.

Figure 8A:
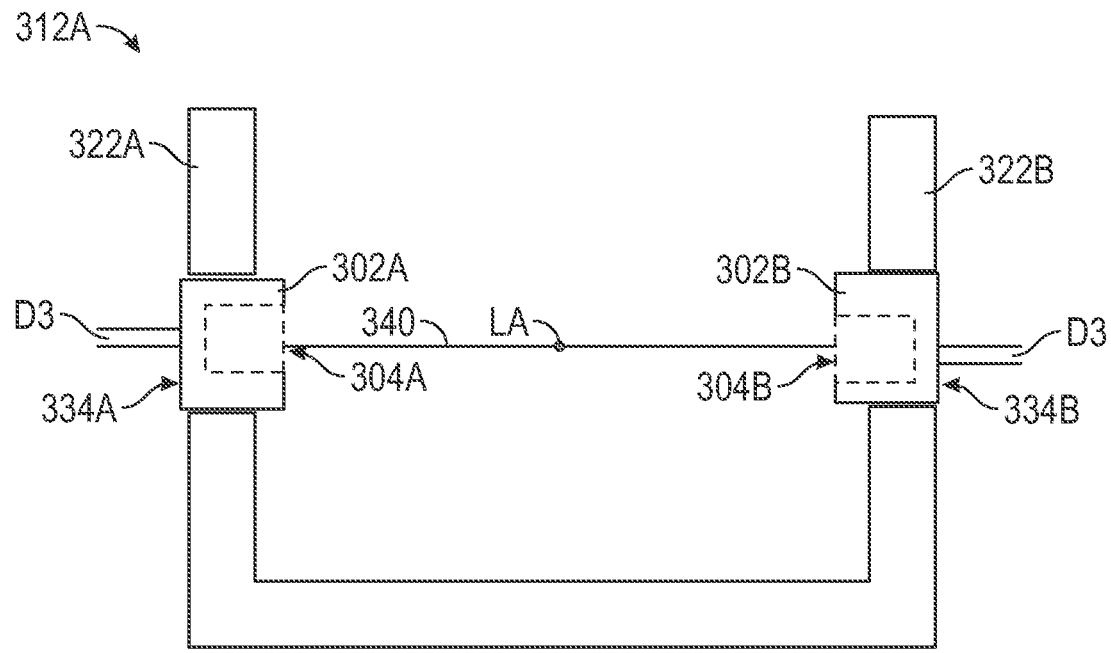
FIG. 8A is a schematic cross-sectional view of another example of a jaw illustrating an offset between journals coupled to the first flange and the second flange according to an example of the present application.
Figure 8B:
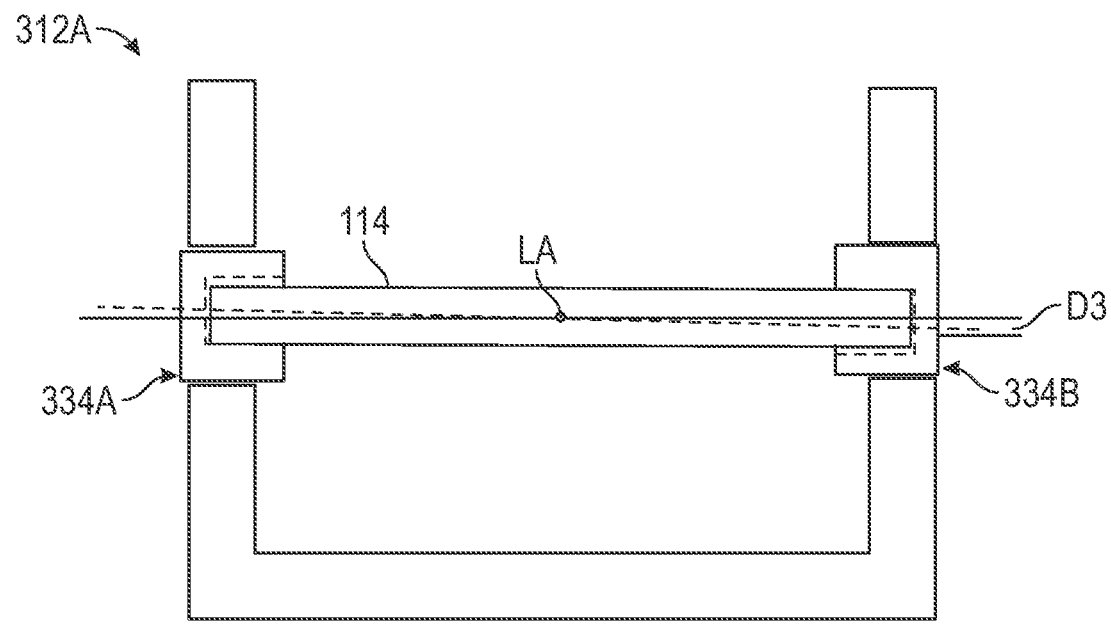
FIG. 8B is a schematic cross-sectional view of the arrangement of FIG. 8A further illustrating a misalignment of a pivot pin that results from the offset of the journals of FIG. 8A according to an example of the present application.

FIGS. 8A-8B provide an example of a jaw 312A that utilizes journals 302A and 302B. Rather than having a first flange 322A and second flange 322B configured in a different manner from one another with either an offset first aperture relative to a second aperture or an offset first slot relative to a second slot, the first flange 322A and second flange 322B have substantially a same shape as illustrated in FIGS. 8A and 8B.

FIGS. 8A and 8B show the journals 302A and 302B can be configured in a different manner from one another to provide an offset/misalignment. More particularly, FIG. 8A shows the apertures 304A and/or 304B of the journals 302A and 302B can be configured to provide the offset of a distance D3 between a central axis of the first aperture 304A and the second aperture 304B and relative to and along the longitudinal axis LA. The distance D3 of the offset can be relative to and along an axis 340 transverse to the longitudinal axis LA as indicated in FIG. 8A. It should be noted that although the journals 302A and 302B are illustrated being used with the first aperture 334A and a second aperture 334B, respectively, in FIGS. 8A and 8B. However, according to other examples journals, bearing, liners or the like, can be utilized with the first and second slots in a similar manner as those illustrated previously.

Figure 9:
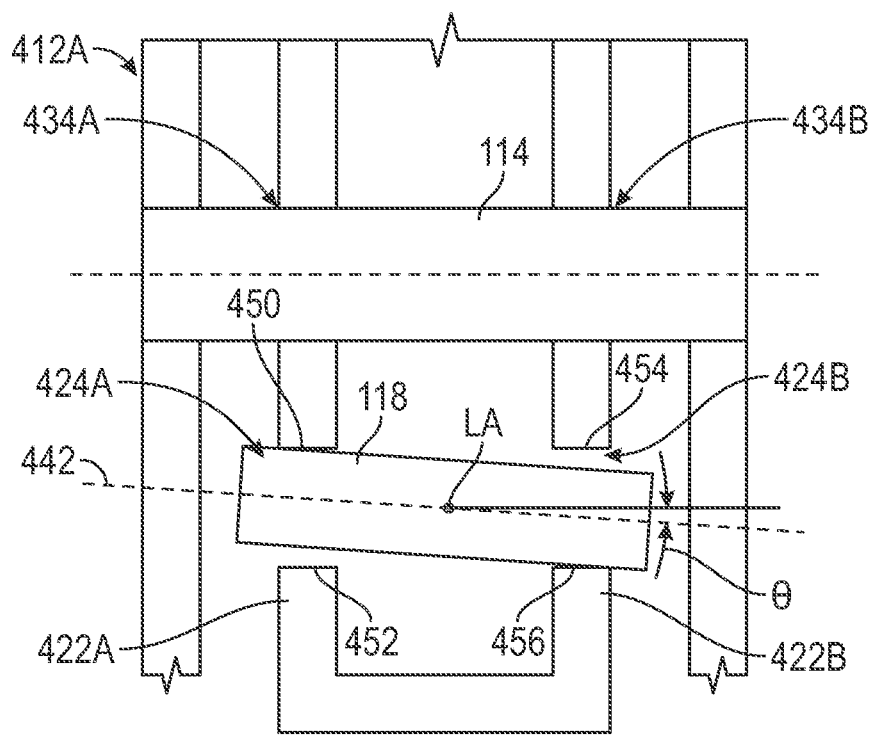
FIG. 9 is a schematic cross-sectional view of another example of a jaw illustrating misalignment of a cam pin relative to a pivot pin within the first flange and the second flange of the jaw according to an example of the present application.

FIG. 9 illustrates in a schematic manner a jaw 412A configured with the cam pin 118 misaligned (e.g., angled) relative to the pivot pin 114. This angle can be measured in the plane that is perpendicular to the longitudinal axis LA. With the arrangement of FIG. 9, the pins 114, 118 can be angled by having the cam pin 118 askew from a plane perpendicular to the longitudinal axis LA along the length or a portion of the length of the longitudinal axis LA. This arrangement should be contrasted to that of FIGS. 1A-2A where the pivot pin 114 and the cam pin 118 are arranged parallel with one another. Put another way, the flanges 422A and 422B of the jaw 412A can be configured in the manner of the flanges 122A and 122B previously described to mirror one another. Thus, the apertures 434A and 434B and the slots 424A and 424B can be of the same configuration, arrangement etc. as those of the apertures 134A and 134B and slots 124A and 124B as previously described. Thus, the features on the first flange 422A of the jaw 412A (including the pivot bore and the cam slot) can be aligned with the features on the second flange 422B of the jaw 412A (including the pivot bore and the cam slot, respectively) relative to the longitudinal axis LA of the jaw 412A. Such misalignment/angulation can be a performed by the inner shaft 116 (FIG. 1A), which could be clocked or otherwise oriented inside the outer shaft 104 (FIG. 1A).

However, in the arrangement of FIG. 9, the cam pin 118 has been angled/tilted by an angle θ relative to the pivot pin 114. As a result of such arrangement, the cam pin 118 can misaligned to the cam slots 424A and 424B such that play is consumed. Thus, as shown in FIG. 9, the misalignment of the cam pin 118 relative to the pivot pin 114 can cause the cam pin 118 to contact a first longitudinal edge 450 of the first flange 422A that defines a first side of first slot 424A. The cam pin 118 can be spaced from a second longitudinal edge 452 of the first flange 422A that defines a second side (opposing the first side) of the first slot 424A by a gap. Similarly, the cam pin 118 can be spaced from a third longitudinal edge 454 of the second flange 422B that defines a first side of the second slot 424B by a gap. The cam pin 118 can contact a fourth longitudinal edge 456 of the second flange 422B that defines a second opposing side of the second slot 424B. Contact between the cam pin 118 and the edge 450 and the cam pin 118 and the edge 456 can reduce play and wobble of the jaw 412A. The cam pin 118 can still move within the first slot 424A and the second slot 424B because of the clearance between the cam pin 118 and the second longitudinal edge 452 and cam pin 118 the third longitudinal edge 454. Put another way, the configuration of FIG. 9 can result in a longitudinal axis 442 of the cam pin 118 being angled at the angle θ so as not to be positioned transverse to the longitudinal axis LA. Rather, the longitudinal axis 442 can form the acute or obtuse angle θ with the longitudinal axis LA.

Figure 10:
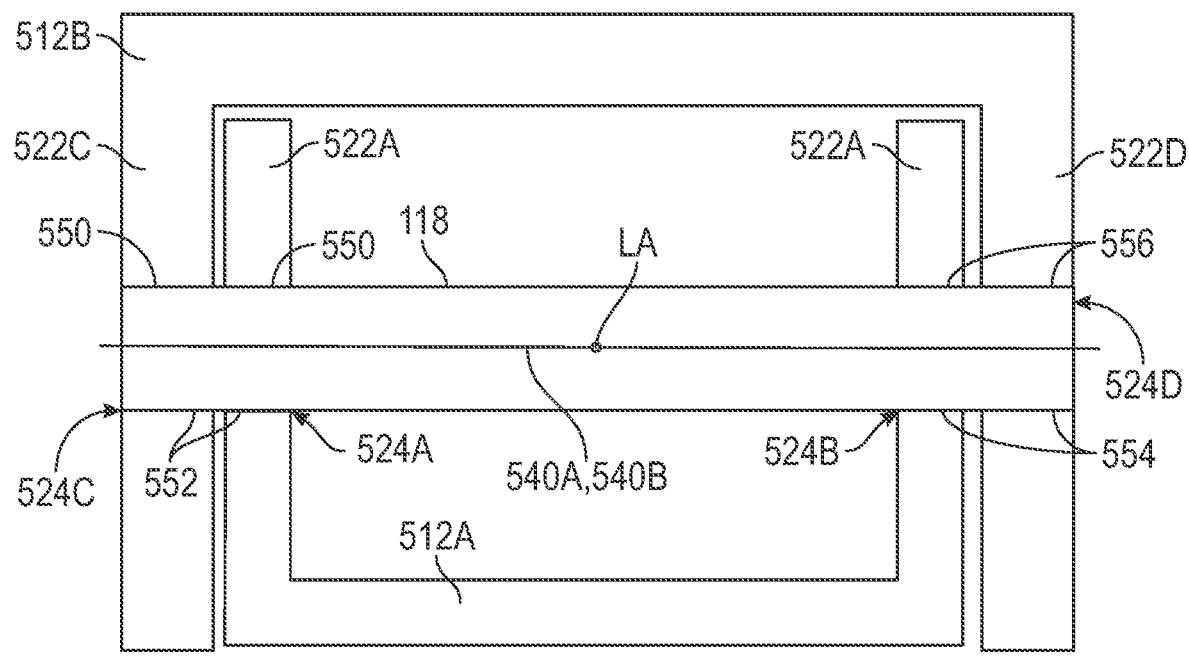
FIG. 10 is a schematic cross-sectional view of the jaws and flanges of FIG. 2 illustrating a first offset in a first cam slot of a first flange of a first jaw from a second cam slot of a second flange of the first jaw and illustrating a second offset in a third cam slot of a third flange of a second jaw from a fourth cam slot of a fourth flange of the second jaw according to an example of the present application.

FIG. 10 shows a schematic arrangement utilizing a second jaw 512B in addition to the first jaw 512A. Such use of two jaws was previously illustrated with the example of FIGS. 1-2. As shown in FIG. 10, the first jaw 512A can be arranged within or adjacent a second jaw 512B. The first jaw 512A can include a first flange 522A and a second flange 522B having one of the configurations previously discussed and illustrated. For example, the first flange 522A and the second flange 522B can have an offset between a first slot 524A and/or a second slot 524B relative to an axis 540A transverse to and intersecting a longitudinal axis LA such as was the case with the examples of FIGS. 4A-6B previously described herein. The second jaw 512B can include a third flange 522C and a fourth flange 522D. The third flange 522C and the fourth flange 522D can have an offset between a third slot 524C and/or a fourth slot 524D relative to an axis 540B transverse to and intersecting a longitudinal axis LA of the first jaw 512A and the second jaw 512B. As shown in FIG. 10, the third flange 522C and the fourth flange 522D can be configured such that a longitudinal axis of the cam pin 118 can be offset from the axis transverse 540B transverse to the longitudinal axis LA. Similarly, the first flange 522A and the second flange 522B can be configured such that the longitudinal axis of the cam pin 118 can be offset from the axis 540A transverse to the longitudinal axis LA. The axes 540A and 540B can be parallel to one another and can align in some configurations.

As shown in FIG. 10, the third flange 522C can be coupled to and form part of the second jaw 512B. The third flange 522C can be arranged to extend substantially parallel to the first flange 522A. The fourth flange 522D can be spaced from the third flange a distance and can be coupled to and form part of the second jaw 512B. The fourth flange 522D can be arranged to extend substantially parallel to the second flange 522B. The cam pin 118 can be moveably secured within the first cam slot 324A and the second cam slot 324B and further the third cam slot 324C and the fourth cam slot 324D. A diameter of the cam pin 118 can be less than a width of both the third cam slot 324C and the fourth cam slot 324D so as to be received by both the third cam slot 324C and the fourth cam slot 324D. Additionally, as was discussed previously, the diameter of the cam pin 118 can be less than a width (as measured between opposing sides) of the first cam slot 324A and the second cam slot 324B.

The configuration of the first flange 522A, the second flange 522B, the third flange 522C and the fourth flange 522D with the offsets discussed above relative to the axes 540A and 540B transverse to the longitudinal axis LA of the first jaw 512A and second jaw 512B can position the cam pin 118 can be spaced from (i.e. have clearance relative to) a first longitudinal edge 550 of the first flange 522A and the third flange 522C that define a first side of the first slot 524A and the third slot 524C by a gap. The cam pin 118 can be in contact with a second longitudinal edge 552 of the first flange 522A and the third flange 522C that define an opposing second side of the first slot 524A and the third slot 524C. Similarly, the cam pin 118 can be in contact with a third longitudinal edge 554 of the second flange 522B and the fourth flange 522D that define a first side of the second slot 524B and the fourth slot 524D. The cam pin 118 can be spaced from a fourth longitudinal edge 556 of the second flange 522B and the fourth flange 522D that define a second opposing side of the second slot 524B and the fourth slot 524D by a gap. Contact between the cam pin 118 and the second longitudinal edge 552 and the cam pin 118 and the third longitudinal edge 554 can reduce play and wobble of the jaws 512A and 512B as previously described.

Various Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A surgical device comprising:
    a first jaw having a longitudinal axis, the first jaw comprising:
        a body portion;
        a first flange coupled to the body portion and defining a first cam slot with a longitudinal extent along the longitudinal axis, the first cam slot including a first longitudinal edge;
        a second flange coupled to the body portion and spaced from the first flange a distance transverse to the longitudinal axis of the first jaw, wherein the second flange has a second cam slot with a longitudinal extent along the longitudinal axis, the second cam slot including a first longitudinal edge; and
        a cam pin moveably secured within the first cam slot and the second cam slot, wherein the cam pin has an increased contact force against the first longitudinal edge of the first cam slot and the first longitudinal edge of the second cam slot along a first portion of the first and second cam slots and a decreased contact force against the first longitudinal edge of the first cam slot and the first longitudinal edge of the second cam slot along a second portion of the first and second cam slots;
    wherein the cam pin is moveably driven back and forth along the longitudinal extent of the first cam slot and the second cam slot with an intentional misalignment of the first cam slot relative to the second cam slot occurring along the first portion of the first and second cam slots.

2. The surgical device of claim 1, wherein the cam pin is spaced from a second longitudinal edge of the first cam slot along the first portion of the first cam slot, and wherein the cam pin is spaced from a second longitudinal edge of the second cam slot along the first portion of the second cam slot.

3. The surgical device of claim 1, wherein the cam pin is positioned relative to the first flange and the second flange such that a longitudinal axis of the cam pin is one of offset from or angled relative to an axis perpendicular to the longitudinal axis of first jaw.

4. The surgical device of claim 3, wherein the first flange is configured to offset at least a portion of the first cam slot in a first direction relative to an axis perpendicular to the longitudinal axis of the first jaw, and wherein the second flange is configured to offset at least a portion of the second cam slot in a second direction, opposite the first direction, relative to an axis perpendicular to the longitudinal axis of the first jaw.

5. The surgical device of claim 1, wherein the first flange has a first aperture spaced from the first cam slot and the second flange has a second aperture spaced from the second cam slot, wherein the first aperture and the second aperture are configured to receive a pivot pin that defines a pivot axis for the first jaw to pivot between a first position and a second position, and wherein the first aperture is offset relative to the second aperture by a distance in a direction that is transverse to the longitudinal axis of the first jaw.

6. The surgical device of claim 1, wherein the first flange has a first aperture spaced from the first cam slot and the second flange has a second aperture spaced from the second cam slot, wherein the first aperture and the second aperture are configured to receive a pivot pin that defines a pivot axis for the first jaw to pivot between a first position and a second position, and wherein the pivot axis is arranged at a non-parallel orientation with respect to the longitudinal axis of the cam pin.

7. The surgical device of claim 1, further comprising a second jaw, wherein the second jaw has a third flange and a fourth flange that are positioned within and generally parallel with the first flange and the second flange, respectively, wherein the third flange includes a third cam slot and the fourth flange includes a fourth cam slot, wherein the cam pin is moveably secured in the third cam slot and the fourth cam slot.

8. The surgical device of claim 7, further comprising:
    a handpiece configured with one or more actuators;
    a tube coupled to the first and second jaws via a pivot pin that defines a pivot axis for the first jaw about the first flange and the second flange and the second jaw about the third flange and the fourth flange; and
    a shaft arranged inward of the tube, wherein the shaft is configured to move the cam pin back and forth within the first cam slot, the second cam slot, the third cam slot and the fourth cam slot to drive the first and second jaws between an open position and a closed position.

9. A surgical device comprising:
    a first jaw having a longitudinal axis;
    a first flange coupled to the first jaw and having a first cam slot and a first aperture spaced from the first cam slot;
    a second flange spaced from the first flange by a distance and coupled to the first jaw, wherein the second flange has a second cam slot and a second aperture spaced from the second cam slot; and
    a cam pin moveably secured within the first cam slot and the second cam slot;
    wherein the first flange has a different configuration than the second flange with regard to at least one of a shape or a position of the first cam slot with respect to a shape or a position of the second cam slot and relative to the longitudinal axis of the first jaw, wherein the different configuration of the first flange relative to the second flange and relative to the longitudinal axis creates an intentional misalignment of the first cam slot relative to the second cam slot that results in an increased contact force between the cam pin and a first edge of the first flange for at least a portion of a longitudinal extent of the first cam slot and a first edge of the second flange for at least a portion of a longitudinal extent of the second cam slot.

10. The surgical device of claim 9, wherein the cam pin is positioned relative to the first flange and the second flange having the increased contact force against a first longitudinal edge of the first cam slot and a first longitudinal edge of the second cam slot along a first portion of the first and second cam slots and a decreased contact force against the first longitudinal edge of the first cam slot and the first longitudinal edge of the second cam slot along a second portion of the first and second cam slots.

11. The surgical device of claim 10, wherein the cam pin is spaced from a second longitudinal edge of the first cam slot along the first portion of the first cam slot, and wherein the cam pin is spaced from a second longitudinal edge of the second cam slot along the first portion of the second cam slot.

12. The surgical device of claim 9, wherein the cam pin is positioned relative to the first flange and the second flange such that the longitudinal axis of the cam pin is one of offset from or angled relative to an axis perpendicular to the longitudinal axis of the first jaw.

13. The surgical device of claim 9, wherein the first flange is configured to offset at least a portion of the first cam slot in a first direction relative to an axis perpendicular to the longitudinal axis of the first jaw and the second flange, and wherein the second flange is configured to offset at least a portion of the second cam slot in a second direction, opposite the first direction, relative to an axis perpendicular to the longitudinal axis of the first jaw.

14. A surgical device comprising:
a first jaw having a longitudinal axis, the first jaw having a first cam slot with a longitudinal extent along the longitudinal axis;
a second jaw; and
a cam pin moveably secured within the first cam slot and having a longitudinal axis with the cam pin positioned relative to the first jaw such an intentional interference between the cam pin and the first jaw in the first cam slot is created toward and to a jaw closed position for the first jaw relative to the second jaw, the intentional interference between the cam pin and the first jaw reduces a wobble of the first jaw toward and to the jaw closed position, wherein a centerline axis of the first cam slot is one of angled or offset relative to the longitudinal axis of the cam pin such that the cam pin is misaligned with the first cam slot to create the intentional interference between the cam pin and the first jaw.

15. The surgical device of claim 14, wherein, with the first jaw pivoted to at least a first position and the cam pin is received in the first cam slot with the cam pin spaced from a first edge of the first jaw that defines a first side of the first cam slot but contacts a second edge of the first jaw that defines a second side of the first cam slot.

16. The surgical device of claim 14, wherein the first jaw has a first aperture spaced from the first cam slot, wherein the first aperture is configured to receive a pivot pin that defines a pivot axis for the first jaw to pivot between a first position and a second position, and wherein the pivot axis is oriented at a non-parallel orientation with respect to the longitudinal axis of the cam pin so as to create the intentional interference between the cam pin and the first jaw.

17. The surgical device of claim 14, wherein the first jaw comprises:
a body portion;
a first flange coupled to the body portion and defining the first cam slot with a longitudinal extent along the longitudinal axis; and
a second flange coupled to the body portion and spaced from the first flange a distance transverse to the longitudinal axis of the first jaw, wherein the second flange defines a second cam slot with a longitudinal extent along the longitudinal axis; and
the cam pin is moveably secured within the first cam slot and the second cam slot, wherein the cam pin is positioned relative to the first flange such that a centerline axis of the second cam slot is angled relative to the longitudinal axis of the cam pin such that the cam pin is misaligned with the second cam slot to create the intentional interference between the cam pin and the first jaw.

* * * * *